US007550615B2

(12) United States Patent
Maruyama et al.

(10) Patent No.: US 7,550,615 B2
(45) **Date of Patent: *Jun. 23, 2009**

(54) PREPARATION PROCESS OF DIGLYCERIDE-RICH FAT OR OIL

(75) Inventors: Eizo Maruyama, Kamisu (JP); Keiji Shibata, Kamisu (JP); Hiroaki Yamaguchi, Kamisu (JP)

(73) Assignee: Kao Corporation, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 11/937,045

(22) Filed: Nov. 8, 2007

(65) Prior Publication Data

US 2008/0071101 A1 Mar. 20, 2008

Related U.S. Application Data

(63) Continuation of application No. 11/313,737, filed on Dec. 22, 2005, now Pat. No. 7,375,240.

(30) Foreign Application Priority Data

Dec. 24, 2004 (JP) ............................ 2004-374267

(51) Int. Cl.
*C11B 3/14* (2006.01)
*C07C 51/43* (2006.01)

(52) U.S. Cl. ...................................... 554/175; 554/211

(58) Field of Classification Search ................. 554/175, 554/211

See application file for complete search history.

(56) References Cited

U.S. PATENT DOCUMENTS

| | | | | |
|---|---|---|---|---|
| 4,443,379 | A * | 4/1984 | Taylor et al. | 554/191 |
| 4,502,948 | A * | 3/1985 | Tabler | 208/183 |
| 4,599,143 | A | 7/1986 | Stage | |
| 4,613,410 | A | 9/1986 | Rivers, Jr. | |
| 4,810,330 | A * | 3/1989 | Stage | 203/4 |
| 4,971,660 | A | 11/1990 | Rivers, Jr. | |
| 5,104,587 | A * | 4/1992 | Besserman et al. | 554/175 |
| 5,231,201 | A * | 7/1993 | Welsh et al. | 554/191 |

FOREIGN PATENT DOCUMENTS

| | | | |
|---|---|---|---|
| DE | 3323120 | A1 * | 1/1985 |
| DE | 3838932 | C1 * | 4/1990 |
| EP | 0 174 517 | A1 | 3/1986 |
| GB | 2 190 095 | A | 11/1987 |
| JP | 59-068398 | | 4/1984 |
| JP | 4-261497 | | 9/1992 |
| JP | 10088183 | A | 4/1998 |
| JP | 11-293276 | | 10/1999 |

* cited by examiner

*Primary Examiner*—Porfirio Nazario-Gonzalez
*Assistant Examiner*—Yate' K Cutliff
(74) *Attorney, Agent, or Firm*—Oblon, Spivak, McClelland, Maier & Neustadt, P.C.

(57) ABSTRACT

Provided is a preparation process of a diglyceride-rich fat or oil, which includes bringing a fat or oil containing diglycerides in an amount of 50 mass % or greater and having a transition metal content of 5 ppm or less into contact with steam while forming a thin film of the fat or oil. This process makes it possible to prepare a diglyceride-rich fat or oil having a reduced odor and good color efficiently.

19 Claims, No Drawings

PREPARATION PROCESS OF DIGLYCERIDE-RICH FAT OR OIL

This is a continuation of U.S. application Ser. No. 11/313,737, filed Dec. 22, 2005.

FIELD OF THE INVENTION

The present invention relates to a preparation process of a diglyceride-rich fat or oil.

BACKGROUND OF THE INVENTION

Fats or oils containing a high concentration of diglycerides are widely used as edible oils because they have pharmacological actions such as a body fat burning action. Diglyceride-rich fats or oils prepared in the conventional manner contain impurities such as fatty acids, monoglycerides and odor components, so that when the diglyceride-rich fats or oils are used as an edible oil, a step of removing these impurities therefrom is necessary for improving its taste. It is common practice to carry out the so-called deodorizing operation, that is, the operation of bringing a fat or oil into contact with steam under conditions of a high temperature and reduced pressure (JP-B-1991-7240).

SUMMARY OF THE INVENTION

In the present invention, there is thus provided a preparation process of a diglyceride-rich fat or oil, which includes bringing a fat or oil containing diglycerides in an amount of 50 mass % or greater and having a transition metal content of 5 ppm or less into contact with steam while forming a thin film of the fat or oil.

DETAILED DESCRIPTION OF THE INVENTION

When an ordinary deodorizing operation is carried out at a low temperature, the effect of distilling off the impurities is so small that the diglyceride-rich fat or oil thus obtained has little improved taste and some fatty acids and monoglycerides remains. Distillation at a higher temperature to remove the impurities, on the other hand, causes a disproportionation reaction, which may lead to problems such as the formation of monoglycerides and triglycerides and the reduction in the diglyceride content and also an undesirable increase in the amount of trans fatty acids.

It is necessary to carry out a deodorizing operation of a diglyceride-rich fat or oil not at a high temperature but at a medium temperature, in order to maintain the high purity of diglycerides and suppress the generation of trans fatty acids attributed to high temperatures. As a result, it took long hours to complete the deodorizing operation.

Unlike the deodorization of triglyceride-rich fats or oils, deodorization of diglyceride-rich fats or oils involves problems such as the undesirable formation of monoglycerides as an impurity component owing to the disproportionation reaction in the deodorizing step and competitive removal of them by distillation. In addition, diglycerides have a weaker hydrophobic property than triglycerides, so that they have a greater affinity to fatty acids and monoglycerides. This makes it difficult to distill off these impurities. It is therefore desired that distillation be carried out at a high temperature as possible, in order to distill off the impurities from the diglyceride-rich fats or oils.

Thus, the diglyceride-rich fats or oils have had a problem that they are more likely to decrease their diglyceride content drastically with an increase in the removing rate of impurities such as odor components, than triglyceride-rich fats or oils. The present invention therefore provides a process of preparing, with high efficiency, a diglyceride-rich fat or oil having less odor, favorable color and a good taste without causing a disproportionation reaction.

The present inventors have carried out various investigations on the steam distillation operation of diglyceride-rich fats or oils and treatment prior thereto. As a result, it has been found that although positive addition of a metal content in the preparation step of a fatty acid is effective for improving the color, heat resistance and odor of it (JP-A-1998-88183), the benefits of the present invention can be attained, contrary to the case of the fatty acid, by using a fat or oil having a transition metal content of 5 ppm or less and bringing the fat or oil into contact with steam while forming a thin film of the fat or oil for the preparation of a diglyceride-rich fat or oil. In short, the present invention makes it possible to efficiently prepare a diglyceride-rich fat or oil having substantially no odor, a good color and an improved taste by treatment in a short time.

The fat or oil employed in the process of the present invention contains diglycerides in an amount of 50 mass % or greater. From the standpoint of its use as an edible oil, the fat or oil contains diglycerides preferably in an amount of 60 mass % or greater, more preferably in an amount of 80 mass % or greater. Such a fat or oil containing diglycerides in an amount of 50 mass % or greater is obtainable by the esterification reaction between a fatty acid derived from a fat or oil and glycerin, or the ester exchange reaction between a fat or oil and glycerin. Either reaction is preferably conducted under enzymatically mild conditions while using a 1,3-regiospecific lipase or the like in order to prepare a diglyceride-rich fat or oil having an excellent taste.

Either a vegetable fat or oil or animal fat or oil may be used as a raw material for the preparation of the fat or oil containing diglycerides in an amount of 50 mass % or greater. Specific examples of the raw material include rapeseed oil, sunflower oil, corn oil, soybean oil, rice oil, safflower oil, cotton seed oil, beef tallow, linseed oil and fish oil.

In the present invention, a transition metal content in the fat or oil containing diglycerides in an amount of 50 mass % or greater needs to be 5 ppm or less. When the transition metal content in the fat or oil exceeds 5 ppm, a sufficient deodorizing effect is not attained even if the fat or oil is brought into contact with steam while forming a thin film, thus resulting in the failure to provide a good color and taste. In addition, the disproportionation reaction is not suppressed. The transition metal content is more preferably 2 ppm or less, even more preferably 1 ppm or less. Examples of the transition metal include iron, copper, lead, nickel, chromium, zinc, aluminum, tin, gold and platinum.

When the transition metal content in the fat or oil containing diglycerides in an amount of 50 mass % or greater exceeds 5 ppm, on the other hand, it is necessary to reduce it to 5 ppm or less in advance. The transition metal content in the fat or oil can be reduced to 5 ppm or less preferably by adopting an adsorption method using an adsorbent, chromatography, or treatment with a chelating agent. Examples of the adsorption method include a method using activated clay, acid clay, silica gel, zeolite, activated carbon or ion exchange resin as an adsorbent. For example, the fat or oil is mixed with such an adsorbent and then, the resulting mixture is separated into the adsorbent and the fat or oil by filtration, or the fat or oil is circulated in an adsorption column filled with the adsorbent.

Chromatography is performed, for example, by a method using an organic solvent and zeolite as an eluent and fixed bed, respectively. More specifically, it is performed by simulated moving bed technology.

Examples of the treatment with a chelating agent include a method of adding a chelating agent to a fat or oil and then washing the resulting mixture with water; and a method of adding a chelating agent to a fat or oil and then subjecting the resulting mixture to absorption treatment. Examples of the chelating agent include citric acid, succinic acid, maleic acid, oxalic acid, aconitic acid, itaconic acid, citraconic acid, tartaric acid, fumaric and malic acid. Use of citric acid or succinic acid is preferred from the standpoints of economy and metal content removing performance. Such a chelating agent is used preferably in an amount of from 0.02 to 5 mass %, more preferably from 0.05 to 1 mass % in the fat or oil. In the method of adding a chelating agent, followed by washing with water, it is preferred, from the standpoints of economy and metal content removing performance, to continuously mix the chelating agent and fat or oil in a line mixer and continuously separating the mixture into a light liquid and a heavy liquid by a centrifugal separator. In the method of adding a chelating agent, followed by adsorption treatment, use of activated carbon as an adsorbent is preferred from the standpoints of economy and metal content removing performance.

In the process of the present invention, the fat or oil having a transition metal content of 5 ppm or less is brought into contact with steam while forming a thin film. From the standpoints of maintaining the purity of diglycerides, improving the removing capacity of impurities and improving the taste, it is preferred to cause the fat or oil to flow downward through a distillation column filled with a structured packing material and then circulate steam so as to countercurrently bring it into contact with the fat or oil. When the fat or oil is caused to flow downward through the distillation column filled with a structured packing material, it forms a thin film because it flows down over the surface of the packing material.

The fat or oil and steam are brought into contact with each other preferably under the following conditions in consideration of economy, deodorization efficiency and quality. The temperature of the fat or oil is preferably from 240 to 280° C., more preferably from 250 to 280° C., even more preferably from 260 to 280° C.; the contact time is preferably from 1 to 15 minutes, more preferably from 1 to 10 minutes, even more preferably from 2 to 10 minutes; the pressure is preferably from 0.02 to 2 kPa, more preferably from 0.05 to 1 kPa, even more preferably from 0.1 to 0.8 kPa; and the amount of steam is preferably from 0.1 to 10 mass %, more preferably from 0.2 to 5 mass %, even more preferably from 0.2 to 2 mass % based on the amount of the fat or oil.

The flow rate of the fat or oil is preferably from 1 to 20 ton/h, more preferably from 2 to 10 ton/h per unit cross-sectional area ($m^2$) of the packing material in view of the stability of the deodorizing operation, deodorization efficiency and productivity.

The structured packing material is preferably a regular packing material having a specific surface area of from 200 to 700 $m^2/m^3$.

The diglyceride-rich fat or oil treated by the process of the present invention has been deodorized and at the same time exhibits good color. In addition, the amount of trans fatty acids which are by-products of the treatment is small and the reduction in a diglyceride content is also small.

The following examples further describe and demonstrate embodiments of the present invention. The examples are given only solely for the purpose of illustration and are not to be construed as limitations of the present invention.

EXAMPLES

Preparation of Raw Material Fat or Oil

Esterification reaction between 100 parts by mass of a 7:3 (mass ratio) mixture of soybean oil fatty acid and rapeseed oil fatty acid and 15 parts by mass of glycerin was performed using an enzyme. The esterification product thus obtained was subjected to molecular distillation to remove the fatty acid and monoglyceride to provide a raw material fat or oil A. To the raw material fat or oil A was added a 30% aqueous solution of citric acid in an amount of 0.8 mass % based on the fat or oil at 90° C., followed by mixing at 90° C. and 1 kPa for 1 hour. After addition of 10 mass % of water to the resulting fat or oil, an oil-water separation operation was repeated three times to provide a raw material fat or oil B.

An esterification reaction between 100 parts by mass of a fatty acid derived from linseed oil and 15 parts by mass of glycerin was performed using an enzyme. The esterification product thus obtained was subjected to molecular distillation to remove the fatty acid and monoglyceride. To the resulting fat or oil was added a 30% aqueous solution of citric acid in an amount of 0.8 mass %, based on the fat or oil, at 90° C., followed by mixing at 90° C. and 1 kPa for 1 hour. After the addition of water to the fat or oil in an amount of 10 mass %, an oil-water separating operation was repeated three times to provide a raw material fat or oil C. The physical properties of these raw material fats or oils are shown in Table 1. The transition metal content was measured by ICP mass spectrometry. The composition of the fat or oil was determined by gas chromatography.

TABLE 1

| | Derived from | Transition metal (ppm) | FFA (wt %) | MAG (wt %) | DAG (wt %) | Trans unsaturated fatty acid(wt %) | Color |
|---|---|---|---|---|---|---|---|
| Raw material fat or oil A | Soybean/rapeseed | 20 | 1.31 | 1.96 | 84.4 | 2.6 | 14.2 |
| Raw material fat or oil B | Soybean/rapeseed | 0.1 | 1.31 | 1.96 | 84.4 | 2.6 | 14.2 |
| Raw material fat or oil C | Linseed | 0.1 | 0.86 | 1.46 | 85.1 | 4.1 | 37.1 |

FFA: Free fatty acid
MAG: Monoglycerides
DAG: Diglycerides

Example 1

By using a deodorization column equipped inside thereof with a regular packing material having a specific surface area of 250 $m^2/m^3$ under the conditions of a temperature of 250° C., column top pressure of 0.3 kPa and steam amount of 0.55 mass % based on the amount of fat or oil, the raw material fat or oil B was deodorized by causing it to flow in the column at a flow rate of 3.7 ton/$m^2$/Hr (flow rate of the fat or oil per cross-sectional area of the column) so that steam and the fat or oil are brought into contact with each other countercurrently. An average contact time of the fat or oil and steam over the packing material was 10 minutes. The composition of the fat or oil was found by gas chromatography. The color was measured using a 133.4 mm cell in the A.O.C.S. Cc-13e-92 (Lovibond method) and it was evaluated by the value obtained by adding Y to 10×R, that is, 10R+Y wherein R represents the value of Red and Y represents the value of Yellow. The taste was evaluated organoleptically based on the below-described standards. Results are shown in Table 2.

[Evaluation criteria of taste]
A: Excellent taste
B: Good taste
C: Little inferior in taste
D: Inferior in taste Example 2

In a similar manner to that employed in Example 1 except that the deodorization temperature was raised to 260° C., the fat or oil was deodorized. The results are shown in Table 2.

Example 3

In a similar manner to Example 1 except that the deodorization temperature was raised to 270° C., the flow rate of a fat or oil was increased to 7.4 ton/$m^2$/Hr, and the contact time was reduced to 5 minutes, the fat or oil was deodorized. The results are shown in Table 2.

Example 4

The raw material fat or oil C was deodorized by using a deodorization column equipped inside thereof with a regular packing material having a specific surface area of 700 $m^2/m^3$ under the conditions of a temperature of 270° C., column top pressure of 0.3 kPa, and amount of steam of 2 mass % based on the amount of the fat or oil and causing the fat or oil to flow in the column at a flow rate of 1.3 ton/$m^2$/Hr (flow rate per cross-sectional area of the column). The results are shown in Table 2.

Comparative Example 1

The raw material fat or oil A was charged in a tray type deodorization vessel and deodorized for 1 hour under the conditions of temperature of 240° C., pressure of 0.4 kPa and amount of steam of 3% based on the amount of the fat or oil. The deodorization was performed by batch-wisely blowing a predetermined amount of steam into the deodorization vessel charged with the raw material fat or oil. The results are shown in Table 2.

Comparative Example 2

The raw material fat or oil B was charged in a tray type deodorization vessel and deodorization was performed in a similar manner to that employed in Comparative Example 1. The results are shown in Table 2.

Comparative Example 3

The raw material fat or oil C was charged in a tray type deodorization vessel and deodorization was performed for 2 hours in a similar manner to that employed in Comparative Example 1 under the conditions of a temperature of 230° C., amount of steam of 3% based on the amount of the fat or oil and vacuum degree of 0.4 kPa. The results are shown in Table 2.

TABLE 2

| | Raw material fat or oil used | Deodorizing temperature (° C.) | Flow rate (ton/$m^2$/hr) | FFA (wt %) | MAG (wt %) | DAG (wt %) | Trans unsaturated fatty acid (wt %) | Taste | Color |
|---|---|---|---|---|---|---|---|---|---|
| Ex. 1 | B | 250 | 3.7 | 0.27 | 0.61 | 86.1 | 3.1 | B | 16.9 |
| Ex. 2 | B | 260 | 3.7 | 0.05 | 0.19 | 84.9 | 3.2 | A | 14.2 |
| Ex. 3 | B | 270 | 7.4 | 0.05 | 0.4 | 84.0 | 3.1 | A | 11.3 |
| Ex. 4 | C | 270 | 1.3 | 0.06 | 0.1 | 85.0 | 4.7 | A | 25.9 |
| Comp. Ex. 1 | A | 240 | — | 0.25 | 4.9 | 41.2 | 3.6 | B | 13 |
| Comp. Ex. 2 | B | 240 | — | 0.1 | 1.5 | 82.5 | 3.6 | B | 13 |
| Comp. Ex. 3 | C | 230 | — | 0.11 | 0.9 | 84.4 | 6.2 | B | 34.9 |

As evidenced from the above-described results, it is possible to efficiently obtain a diglyceride-rich fat or oil having a good taste and color by bringing the fat or oil having a transition metal content of 5 ppm or less into contact with steam while forming a thin film of the fat or oil.

The invention claimed is:

1. A process comprising bringing a fat or oil which comprises diglycerides in an amount of 50 mass % or greater and a transition metal, the transition metal content being 5 ppm or less, into contact with steam while forming a thin film of the fat or oil.

2. The process according to claim 1, wherein the fat or oil is brought into contact with steam while forming a thin film by a method of causing the fat or oil to flow downwards in a distillation column filled with a structured packing material and flowing steam so as to countercurrently bring the steam into contact with the fat or oil.

3. The process according to claim 1, wherein the fat or oil and steam are brought into contact with each other under the conditions of the fat or oil temperature of from 250 to 280° C. for 1 to 15 minutes.

4. The process according to claim 1, wherein the fat or oil having a transition metal content reduced to 5 ppm or less is employed.

5. The process according to claim 3, wherein the fat or oil having a transition metal content reduced to 5 ppm or less is employed.

6. The process according to claim 4, wherein the transition metal content is reduced by adsorption treatment or a method of adding a chelating agent to the fat or oil and washing the resulting mixture with water.

7. The process according to claim 5, wherein the transition metal content is reduced by adsorption treatment or a method of adding a chelating agent to the fat or oil and washing the resulting mixture with water.

8. The process according to claim 2, wherein the fat or oil and steam are brought into contact with each other under the conditions of the fat or oil temperature of from 250 to 280° C. for 1 to 15 minutes.

9. The process according to claim 2, wherein the fat or oil having a transition metal content reduced to 5 ppm or less is employed.

10. The process according to claim 8, wherein the fat or oil having a transition metal content reduced to 5 ppm or less is employed.

11. The process according to claim 1, wherein the fat or oil comprises diglycerides in an amount of 60 mass % or greater.

12. The process according to claim 1, wherein the fat or oil comprises diglycerides in an amount of 80 mass % or greater.

13. The process according to claim 1, wherein the transition metal content is 2 ppm or less.

14. The process according to claim 1, wherein the transition metal content is 1 ppm or less.

15. The process according to claim 14, wherein the fat or oil and steam are brought into contact with each other under the conditions of the fat or oil temperature of from 250 to 280° C. for 1 to 15 minutes.

16. The process according to claim 14, wherein the fat or oil having a transition metal content reduced to 5 ppm or less is employed.

17. The process according to claim 14, wherein the transition metal content is reduced by adsorption treatment or a method of adding a chelating agent to the fat or oil and washing the resulting mixture with water.

18. The process according to claim 14, wherein the fat or oil comprises diglycerides in an amount of 60 mass% or greater.

19. The process according to claim 14, wherein the fat or oil comprises diglycerides in an amount of 80 mass% or greater.

* * * * *